United States Patent [19]

Kawamura et al.

[11] Patent Number: 5,359,097
[45] Date of Patent: Oct. 25, 1994

[54] PROCESS FOR PREPARATION OF GLYCIDYL ETHER

[75] Inventors: Kiyoshi Kawamura, Niiza; Tomio Ota, Sayama, both of Japan

[73] Assignee: Kowa Company Ltd., Aichi, Japan

[21] Appl. No.: 571,543

[22] PCT Filed: Dec. 25, 1989

[86] PCT No.: PCT/JP89/01293
§ 371 Date: Jul. 18, 1990
§ 102(e) Date: Jul. 18, 1990

[87] PCT Pub. No.: WO90/07506
PCT Pub. Date: Jul. 12, 1990

[30] Foreign Application Priority Data

Dec. 26, 1988 [JP] Japan .................. 63-326205

[51] Int. Cl.$^5$ .................................. C07D 311/04
[52] U.S. Cl. ............................ 549/399; 549/517
[58] Field of Search .................... 549/517, 399

[56] References Cited

U.S. PATENT DOCUMENTS 4,582,892  4/1986  Chang et al. .............. 549/517
4,677,170  6/1987  Monnier et al. ............ 525/539

FOREIGN PATENT DOCUMENTS 126449   11/1984  European Pat. Off. .
0186048  7/1986   European Pat. Off. .
0204659  12/1986  European Pat. Off. .
0306919  3/1989   European Pat. Off. .
0355830  2/1990   European Pat. Off. .
0024578  2/1983   Japan .
2175715  7/1990   Japan .

OTHER PUBLICATIONS

Chemical Abstracts, vol. 110, No. 9, Feb. 27, 1989, p. 507, Abstract No. 73883q.

*Primary Examiner*—C. Warren Ivy
*Assistant Examiner*—A. A. Owens
*Attorney, Agent, or Firm*—Wenderoth, Lind & Ponack

[57] ABSTRACT

A process is provided for preparation of a glycidyl ether represented by the general formula

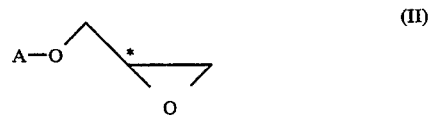

(II)

wherein A represents an aryl group optionally having a substituent or a heteroaryl group optionally having a substituent, and the carbon atom marked with * is an asymmetric carbon, which comprises reacting an aryl alcohol represented by the general formula

A—OH     (I)

wherein A is as defined above, with an epihalohydrin in the presence of a quaternary ammonium salt; and, if necessary, further treating the reaction product with a base. According to the present process, it is possible to prepare by simple procedures and in a high optical purity glycidyl ethers of the above formula (II) useful as an intermediate for preparation of medicines, particularly medicines having β-adrenoreceptor blocking action or the like.

6 Claims, No Drawings

PROCESS FOR PREPARATION OF GLYCIDYL ETHER

TECHNICAL FIELD

This invention relates to a new process for preparation of glycidyl ethers useful as an intermediate for preparation of chemical drugs such as medicines or agricultural chemicals, particularly medicines having a β-adrenoreceptor blocking action or the like.

BACKGROUND OF THE INVENTION

β-adrenoreceptor blocking agents have been widely used for curing or treatment of circulatory system diseases such as hypertension, angina pectoris and arrhythmia, and many of them are aryloxypropanolamines having a structure represented by the following formula

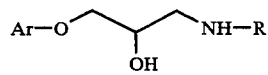

(1)

wherein Ar represents a mother nucleus such as an aryl group and R represents a lower alkyl group or the like.

Various processes for preparation of a compound represented by the above formula (1) have been reported, and a typical one among them is a process shown by the following reaction formula

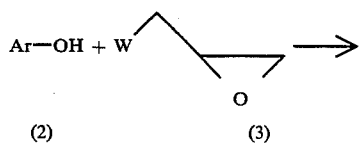

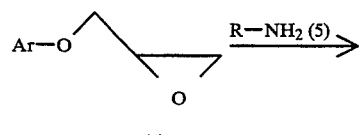

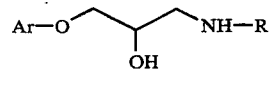

That is, the typical process is a process which comprises making an epoxy compound (3) act on an aryl alcohol (2) to prepare a glycidyl ether (4), and then making an amine (5) act thereon to prepare a desired aryloxypropanolamine (1).

In the above reactions, the reaction of the glycidyl ether (4) with the amine (5) as the second reaction generally proceeds with a good yield without occurrence of side reactions and thus there is no particular problem about the reaction, whereas the reaction of the aryl alcohol (2) with the epoxy compound (3) as the first reaction has, particularly in preparation of an optically active product, problems of lowering of optical purity and the like.

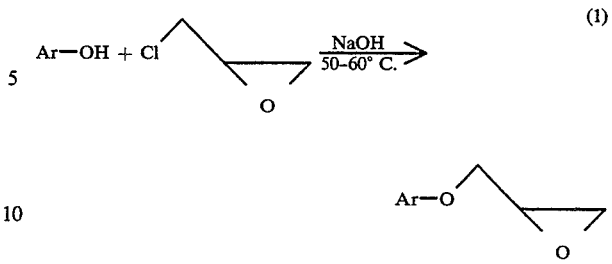

[Please refer to Japanese Patent Publication No. 54317/1986; Japanese Laid-Open Patent Publication No. 167981/1982; J. Med. Chem., 15(3), 260-266(1972); etc.]

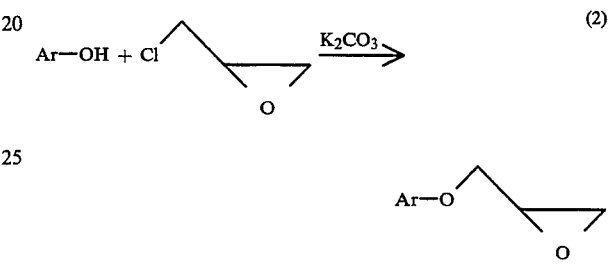

Please refer to J. Am. Chem. Soc., 101, 3666(1979); Chem. Pharm. Bull., 35(9), 3691-3698(1987); etc.]

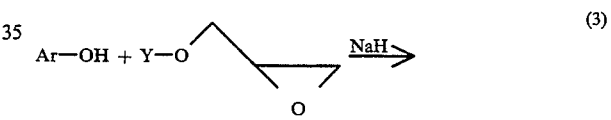

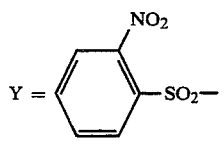

Please refer to Japanese Laid-Open Patent Publication No. 208973/1985; Chem. Pharm. Bull., 35(9), 3691-3698(1987)]

Y=CF$_3$SO$_2$—

Please refer to J. Am. Chem. Soc., 101, 3666(1979)]

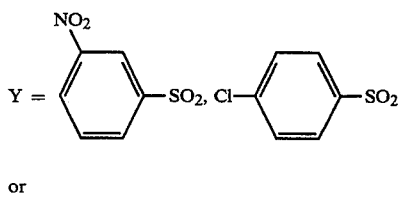

or

-continued

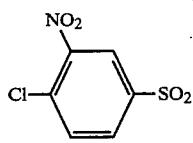

[Please refer to WO190/1988]

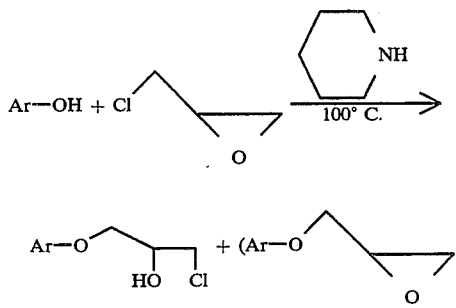

[Please refer to J. Med. Chem., 15(3), 260–266(1972); and J. Med. Chem., 23(10), 1122–1126(1980)]

Among these processes, the processes of the above (1) and (2) are processes wherein heating is carried out in the presence of a base such as sodium hydroxide or potassium carbonate, and thus are not suitable in case an aryl alcohol as a raw material is unstable against the base. For example, in case the raw material is an aryl alcohol having on the mother nucleus (Ar) a nitroxy group, an acylamino group, an alkylaminocarbonylalkoxy group, an alkoxycarbonyl group or the like, there is a drawback that these groups are liable to be eliminated or hydrolyzed by the base. Further, there is another drawback that when these processes are applied to preparation of an optically active product, optical purity of the resulting glycidyl ether is lowered.

On the other hand, in the process of the above (3), lowering of optical purity occurs only to a small extent, but it is necessary to prepare as a raw material an optically active glycidyl sulfonate and thus the process is industrially disadvantageous.

Further, the process of the above (4) has a drawback of low yield and formation of several by-products which are hard to remove.

SUMMARY OF THE INVENTION

The object of this invention is to provide a novel process for preparation of a glycidyl ether which does not have the drawbacks as above-mentioned, brings about only a small lowering of optical purity even when it is applied to preparation of an optically active product, and is capable of preparing the glycidyl ether industrially advantageously and in a high yield.

According to this invention, a process is provided for preparation of a glycidyl ether represented by the general formula

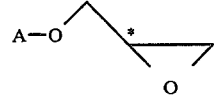

wherein A represents an aryl group optionally having a substituent(s) or a heteroaryl group optionally having a substituent(s), and the carbon atom marked with * is an asymmetric carbon, which comprises reacting an aryl alcohol represented by the general formula

A—OH    (I)

wherein A is as defined above, with an epihalohydrin in the presence of a quaternary ammonium salt; and, if necessary, further treating the reaction product with a base.

DETAILED DESCRIPTION OF THE INVENTION

The process of this invention can be shown by the following reaction formula:

Reaction formula 1

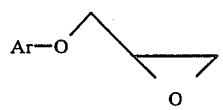

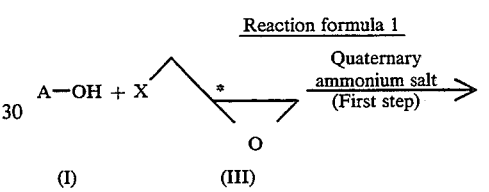

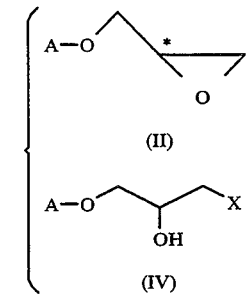

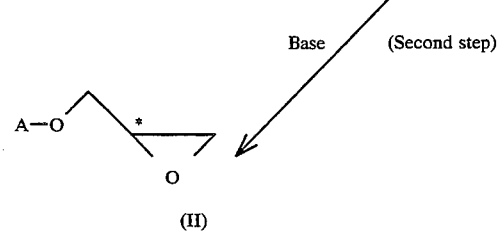

wherein X represents a halogen atom.

In the present specification, the term "lower" means that the group or compound to which this term is attached has 6 or less, preferably 4 or less, carbon atoms. Further, "halogen atom" include fluorine, chlorine, bromine and iodine atoms, and chlorine, bromine and iodine atoms are preferred.

The first step of the process of this invention is a step wherein an aryl alcohol of the formula (I) is reacted with an epihalohydrin of the formula (III), for example epichlorohydrin, epibromohydrin or the like in the presence of a quaternary ammonium salt. Although this reaction can be carried out at an elevated temperature up to about 100° C., a relatively low reaction temperature can usually be used around room temperature or below, for example in the range of about 0° C. to about 40° C., preferably about 15° C. to about 30° C. This reaction can be completed at such a reaction temperature in a time on the order of about 10 to 150 hours. Further, this reaction can be carried out in an organic solvent, for example chloroform, ethyl acetate, tetrahydrofuran, dioxane, acetone or the like, and it is also possible to use the epihalohydrin of the formula (III) as a reaction solvent by using the epihalohydrin in a large excessive amount.

The ratio of an epihalohydrin of the formula (III) to an aryl alcohol of the formula (I) is not critical, and can be varied in a wide range in accordance with the kind of aryl alcohol, etc. Generally, it is suitable to use the epihalohydrin in the range of 1 to 10 moles, preferably 2 to 5 moles per mole of an aryl alcohol of the formula (I).

The characteristic feature of the process of this invention lies in carrying out the reaction of an aryl alcohol of the formula (I) with an epihalohydrin of the formula (III) in the presence of a quaternary ammonium salt as a catalyst. Usable quaternary ammonium salts include those represented by the general formula

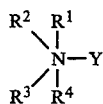 (V)

wherein $R^1$, $R^2$, $R^3$ and $R^4$ and are the same or different and each of them represents a monovalent hydrocarbon group, or optionally two of $R^1$, $R^2$, $R^3$ and $R^4$ may combine to form a heterocyclic ring together with the nitrogen atom to which they are attached; and Y represents a halogen atom.

In this connection, the "monovalent hydrocarbon group" may be any of aliphatic, alicyclic and aromatic ones or a combination thereof. Examples thereof include lower alkyl groups such as methyl, ethyl, n-propyl, isopropyl, n-butyl, isobutyl, sec-butyl, tert-butyl, n-pentyl and n-hexyl groups; aryl groups having 6 to 10 carbon atoms such as phenyl, tolyl and naphthyl; aralkyl groups such as benzyl, phenethyl, naphthylmethyl and naphthylethyl; etc.

Further, examples of a heterocyclic ring which can be formed when two of $R^1$, $R^2$, $R^3$ and $R^4$ combine together with the nitrogen atom to which they are attached, include pyrrolidine, piperidine and morpholine rings, etc.

Further, as specific examples of quaternary ammonium salts usable in this invention the following ones can be mentioned:
tetramethylammonium chloride, tetraethylammonium chloride, tetrapropylammonium chloride, tetrabutylammonium chloride, tetramethylammonium bromide, tetraethylammonium bromide, tetrapropylammonium bromide, tetrabutylammonium bromide, tetramethylammonium iodide, tetraethylammonium iodide, tetrapropylammonium iodide, tetrabutylammonium iodide, isopropyltrimethylammonium bromide, sec-butyltrimethylammonium iodide, pentyltriethylammonium chloride, phenyltrimethylammonium bromide, benzyltrimethyl iodide, dimethylpyrrolidinium chloride, dimethylmorpholinium bromide, etc.

As particularly preferred among the above-mentioned quaternary ammonium salts in this invention, those of the above formula (V) are mentioned wherein $R^1$ to $R^4$ are the same or different and each of them represents a lower alkyl group, namely tetra (lower alkyl) ammonium halide. Particularly preferred among them are tetramethylammonium chloride, tetraethylammonium chloride, tetrapropylammonium chloride, tetrabutylammonium chloride, tetramethylammonium bromide, tetraethylammonium bromide, tetrapropylammonium bromide, tetrabutylammonium bromide, tetramethylammonium iodide, tetraethylammonium iodide, tetrapropylammonium iodide, tetrabutylammonium iodide, etc.

On the other hand, although the halogen (Y) of the quaternary ammonium salt may be any of fluorine, chlorine, bromine and iodine, chlorine, bromine and iodine are especially suitable. Among them iodine is particularly preferred.

In this invention, a quaternary ammonium salt is used in catalytic amount, and can usually be used within the range of 1/50 to ½ mole, preferably 1/20 to 1/5 mole, per mole of an aryl alcohol of the above formula (I).

By the reaction of the above-mentioned first step are formed, as desired products, a glycidyl ether of the above formula (II) and a hydroxypropyl ether of the formula (IV).

Although the formation ratio of a compound of the formula (II) to a compound of the formula (IV) cannot definitely be stated because it depends on reaction conditions, kind of the compound of the formula (I), etc., the molar ratio of the compound of the formula (II)/the compound of the formula (IV) is generally in the range of ⅔ to 1/10.

Although the thus formed glycidyl ether of the formula (II) can be separated from the reaction mixture at the stage of completion of the first step and purified, it is industrially advantageous to subject it successively to the second step without separation.

That is, the reaction can be carried out at a temperature around or lower than room temperature, usually in the range of about −10° to about 30° C., more preferably in the range of about 0° to about 20° C. Examples of usable bases include inorganic alkalis such as sodium hydroxide, potassium hydroxide, sodium carbonate, potassium carbonate and sodium hydride; alcoholates such as sodium methylate and sodium ethylate; 1,8-diazabicyclo-[5.4.0]undec-7-ene; 2,4,6-collidine, 2,6-lutidine, triethylamine, etc. Although the amount of these bases used is not strictly limited, it is generally suitable to use such a base within the range of 0.5 to 5 moles, preferably 1 to 3 moles per mole of the aryl alcohol of the formula (I) used as a starting raw material.

After completion of the reaction, the formed glycidyl ether of the formula (II) can be separated from the reaction mixture and purified, according to methods per se known, for example methods of extraction, crystallization, chromatography, filtration, etc.

The aryl group in compounds of the above formula (I) used as a starting raw material in the process of this invention may either be a monocyclic or polycyclic one, or may further be a condensed ring with an alicyclic ring, and examples thereof include phenyl, naphthyl, tetrahydronaphthyl, indenyl, indanyl groups and the like. Further, the heteroaryl group is a monocyclic or polycyclic aromatic heterocyclic group containing in the aromatic ring at least one, preferably 1 to 3 hetero atoms selected from N, S and O, and examples thereof include indolyl, carbazolyl, 1,3,5-thiadiazolyl, 3,4-dihydrobenzopyranyl, coumaryl, carbostyril, benzofuranyl, etc.

These aryl and heteroaryl groups can optionally have substituent(s). Examples of the substituents include lower alkyl groups such as methyl, ethyl, n-propyl and isopropyl; lower alkenyl groups such as allyl; lower alkoxy groups such as methoxy, ethoxy, n-propoxy, isopropoxy, n-butoxy and t-butoxy; lower alkanoyl groups such as acetyl, propionyl and butyroyl; lower alkoxy lower alkyl groups such as methoxyethyl and ethoxyethyl; lower alkoxycarbonyl groups such as methoxycarbonyl and ethoxycarbonyl; carbamoyl lower alkyl groups such as carbamoylmethyl and carbamoylethyl; mono- or di(lower alkyl)aminocarbonylamino groups such as methylaminocarbonylamino, dimethylaminocarbonylamino and diethylaminocarbonylamino; hydroxyl, cyano and nitroxyl groups; lower alkanoylamino groups such as acetylamino and propionylamino; mono- or di(lower alkyl)aminocarbonyl lower alkoxy groups such as methylaminocarbonylmethoxy, ethylaminocarbonylmethoxy and dimethylaminocarbonylethoxy; a morpholino group; etc. The aryl and heteroaryl groups can have one or two or more of these substituents. Specific examples of the thus substituted aryl and heteroaryl groups are set forth below:

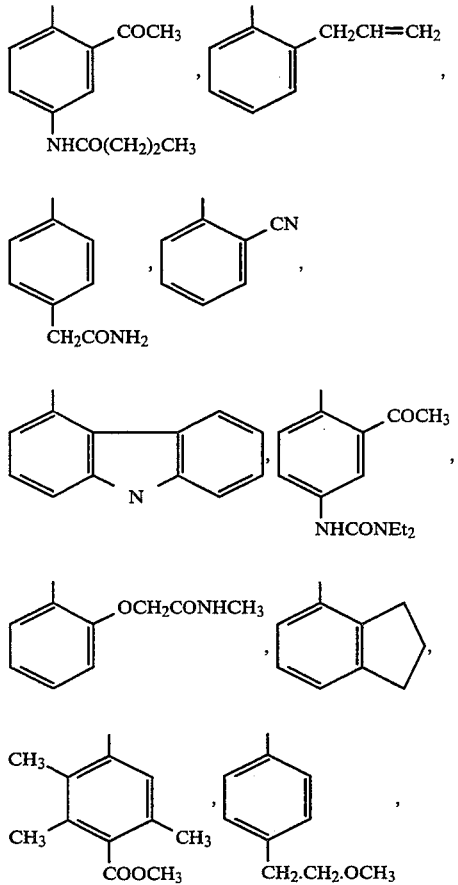

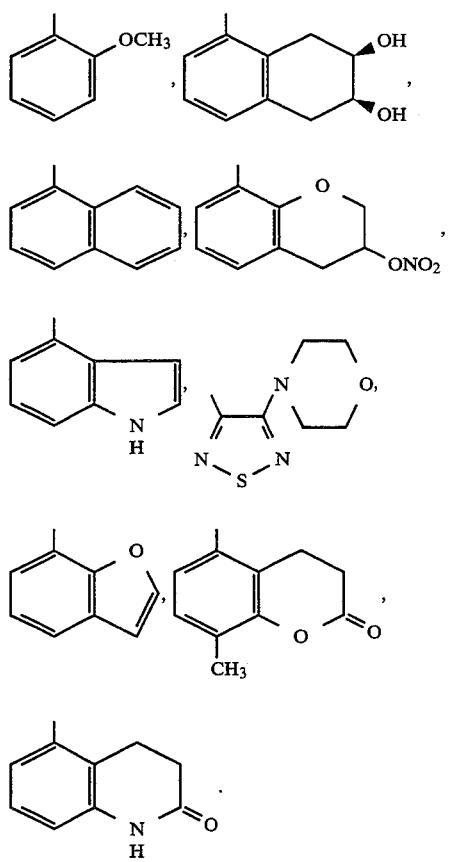

In the reaction of an aryl alcohol with an epihalohydrin (the first step) in the above-described process of this invention, it is not necessary to use a base catalyst such as sodium hydroxide or potassium carbonate which has been necessitated in the usual method, and it is possible to carry out the reaction under a mild condition of a reaction temperature around or below room temperature. Therefore, undesirable side reactions hardly occur and the lowering of optical purity is extremely small, and thus the process is industrially very advantageous. Moreover, since the treatment by a base in the second step can be carried out at a relatively low temperature around or lower than room temperature, the undesirable occurrence of side reactions by use of the base rarely occurs.

Thus, according to the process of this invention it is possible to obtain the optically active desired compound of the formula (II) in a high optical purity by using as an epihalohydrin of the formula (III) an optically active one, and in some occasion using as aryl alcohol of the formula (I) an optically active one.

In the process of this invention, the configuration of the substituent(s) linked to the aromatic nucleus of the aryl alcohol as a starting raw material is maintained substantially as it is, and the configuration of the epihalohydrin is reversed. Therefore, when an aryl alcohol of the formula (I) is reacted with an (R)-epihalohydrin, a compound of the formula (II) having the (S)-type is obtained, whereas when an aryl alcohol of the formula (I) is reacted with an (S)-epihalohydrin, a compound of the formula (II) having the (R)-type is obtained.

In this connection, optically active epihalohydrins used in the process of this invention can be easily prepared microbially, for example according to the method described in Japanese Laid-Open Patent Publication No. 132196/1986 or 40298/1987 or the like.

In preparation of a compound of the afore-mentioned formula (1) as a final useful compound, the step to react an amine in addition to the first and second steps in the preparation process of this invention can be carried out by a one-pot reaction.

EXAMPLE

This invention is further specifically described below according to examples.

EXAMPLE 1

Preparation of 3,4-dihydro-8-(2,3-epoxy)propoxy-3-nitroxy-2H-1-benzopyran 3,4-Dihydro-8-hydroxy-3-nitroxy-2H-1-benzopyran (4.0 g) and 207 mg of tetramethylammonium chloride were added to 5.2 g of epichlorohydrin, and the mixture was stirred at room temperature for 48 hours. After the reaction, a solution of 1.2 g of sodium hydroxide in 60 ml of methanol was added at room temperature under stirring, and the mixture was stirred for 2 hours. A solution of 0.3 g of sulfuric acid in 4 ml of methanol was added to the reaction solution, and after stirring for 5 minutes the solvent was distilled away. The residue was extracted with chloroform and water added, and the chloroform layer was taken, washed with water and dried. Chloroform was distilled away, 30 ml of hexane was added to the residue, and the deposited matter was recovered by filtration, whereby 4.9 g of the desired product (yield 96.8%) was obtained as colorless crystalline powder.

$^1$H-NMR value: δ CDCl$_3$, ppm.

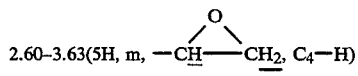
2.60-3.63(5H, m, —CH——CH$_2$, C$_4$—H)

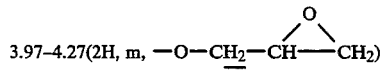
3.97-4.27(2H, m, —O—CH$_2$—CH——CH$_2$)

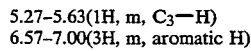
5.27-5.63(1H, m, C$_3$—H)
6.57-7.00(3H, m, aromatic H)

Physicochemical properties of this compound accorded with those of the same compound disclosed in Japanese Laid-Open Patent Publication No. 167981/1982.

EXAMPLE 2

Preparation of (2'S),(3R)-3,4-dihydro-8-(2,3-epoxy)propoxy-3-nitroxy-2H-1-benzopyran (3R)-3,4-Dihydro-8-hydroxy-3-nitroxy-2H-1-benzopyran (700 mng) and 70 mg of tetramethylammonium chloride were added to 920 mg of (R)-epichlorohydrin (optical purity 98% ee or more), and the mixture was stirred at room temperature for 48 hours. A solution of 240 mg of sodium hydroxide in 12 ml of methanol was added to the reaction solution under stirring at room temperature, followed by stirring for 2 hours. Acetic acid (120 mg) was added to the reaction solution, the mixture was stirred for 5 minutes and the solvent was distilled away. The residue was extracted with chloroform and water added, and the chloroform layer was taken and dried. Chloroform was distilled away, and the residue was purified by silica gel column chromatography (solvent: chloroform) and recrystallized from acetone-hexane to obtain 794 mg of the desired product (yield 89.6%) as colorless needle crystals.

Melting point: 127°–128° C.

Specific rotation: $[\alpha]_D^{25}$ +24.7° (c=3, CHCl$_3$)

EXAMPLE 3

Preparation of (2'S),(3S)-3,4-dihydro-8-(2,3-epoxy)propoxy-3-nitroxy-2H-1-benzopyran The same reactions and treatments as in Example 2 were carried out using (3S)-3,4-dihydro-8-hydroxy-3-nitroxy-2H-1-benzopyran, (R)-epichlorohydrin and tetramethylammonium chloride to obtain the desired product.

Yield: 89%

Melting point: 136°–138.5° C.

Specific rotation: $[\alpha]_D^{25}$ −30.5° (c=3, CHCl$_3$)

EXAMPLE 4

Preparation of (2'R),(3R)-3,4-dihydro-8-(2,3-epoxy)propoxy-3-nitroxy-2H-1-benzopyran The same reactions and treatments as in Example 2 were carried out using (3R)-3,4-dihydro-8-hydroxy-3-nitroxy-2H-1-benzopyran, (S)-epichlorohydrin (optical purity 98% ee or more) and tetramethylammonium chloride to obtain the desired product.

Yield: 91.0%

Melting point: 136°–138° C.

Specific rotation: $[\alpha]_D^{25}$ +31.3° (c=3, CHCl$_3$)

EXAMPLE 5

Preparation of (2'R),(3S)-3,4-dihydro-8-(2,3-epoxy)propoxy-3-nitroxy-2H-1-benzopyran The same reactions and treatments as in Example 2 were carried out using (3S)-3,4-dihydro-8-hydroxy-3-nitroxy-2H-1-benzopyran, (S)-epichlorohydrin and tetramethylammonium chloride to obtain the desired product.

Yield: 91.5%

Melting point: 126°–127° C.

Specific rotation: $[\alpha]_D^{25}$ −24.2° (c=3, CHCl$_3$)

EXAMPLE 6

Preparation of (2'S),(3R)-nipradilol[(2'S), (3R)-3,4-dihydro-8-(2-hydroxy-3-isopropylamino)-propoxy-3-nitroxy-2H-1-benzopyran The same reactions and treatments as in Example 2 were carried out using 400 mg of (3R)-3,4-dihydro-8-hydroxy-3-nitroxy-2H-1-benzopyran, 528 mg of (R)-epichlorohydrin and 72 mg of tetrabutylammonium bromide to obtain (2'S),(3R)-3,4-dihydro-8-(2,3-epoxy)-propoxy-3-nitroxy-2H-1-benzopyran. This compound was dissolved, without purification, in 10 ml of methanol, and after addition of 5.2 ml of isopropylamine the mixture was stirred at 75° C. for 1 hour. The reaction solution was treated in a conventional manner, and the resulting crude crystals were purified by silica gel column chromatography [solvent: chloroform-a methanol solution of ammonia (10% w/w)(15:1)] to obtain 550 mg of the desired product (yield 88.9%).

IR value: $\nu_{max}^{KBr}$, cm$^{-1}$ 1620, 1278.

$^1$H-NMR value: δ CDCl$_3$, ppm.
1.07(6H, d, J=6 HZ, CH$_3$)
2.20–3.44(7H, m, C$_4$—H, —CH$_2$NHCH, OH)
3.88–4.12(3H, m, —OCH$_2$CH)
4.12–4.52(2H, m, C$_2$—H)
3.52–5.52(1H, m, C$_3$—H)
6.56–6.92(3H, m, aromatic H)

The IR value and $^1$H-NMR value accorded with those of the same compound disclosed in Chem. Pharm. Bull. 35(9) 3691 to 3698 (1987).

Industrial Applicability

According to the process of this invention, as described above, glycidyl ethers represented by the aforementioned formula (II) useful as an intermediate compound for preparation of medicines can be prepared in a high optical purity by simple procedures, and thus the process is industrially extremely advantageous.

We claim:

1. In a process for preparation of optically active 3,4-dihydro-8-(2,3-epoxy)propoxy-3-nitroxy-2H-1-benzopyran of the formula

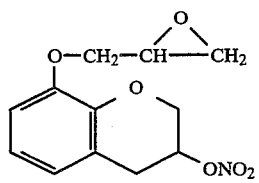

which comprises reacting optically active 3,4-dihydro-8-hydroxy-3-nitroxy-2H-1-benzopyran of the formula

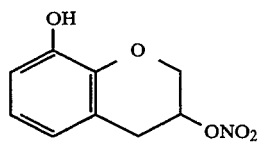

with an optically active epihalohydrin, and further treating the reaction product with a base,
 the improvement which comprises conducting the reaction in the presence of a tetra(lower alkyl) ammonium iodide and at a temperature in the range of about 15° C. to about 30° C.

2. The process of claim 1 wherein the tetra(lower alkyl) ammonium iodide is used in an amount in the range of 1/50 to ½ mole per mole of optically active 3,4-dihydro-8-hydroxy-3-nitroxy-2H-1-benzopyran.

3. The process of claim 1 wherein (3R)-3,4-dihydro-8-hydroxy-3-nitroxy-2H-1-benzopyran is reacted with an (R)-epihalohydrin to prepare (2'S),(3R)-3,4 dihydro-8-(2,3-epoxy)propoxy-3-nitroxy-2H-1-benzopyran.

4. The process of claim 1 wherein (3S)-3,4-dihydro-8-hydroxy-3-nitroxy-2H-1-benzopyran is reacted with an (R)-epihalohydrin to prepare (2'S),(3S)-3,4 dihydro-8-(2,3-epoxy)propoxy-3-nitroxy-2H-1-benzopyran.

5. The process of claim 1 wherein (3R)-3,4-dihydro-8-hydroxy-3-nitroxy-2H-1-benzopyran is reacted with an (S)-epihalohydrin to prepare (2'R),(3R)-3,4 dihydro-8-(2,3-epoxy)propoxy-3-nitroxy-2H-1-benzopyran.

6. The process of claim 1 wherein (3S)-3,4-dihydro-8-hydroxy-3-nitroxy-2H-1-benzopyran is reacted with an (S)-epihalohydrin to prepare (2'R),(3S)-3,4 dihydro-8-(2,3-epoxy)propoxy-3-nitroxy-2H-1-benzopyran.

* * * * *